(12) United States Patent
Bábel

(10) Patent No.: US 11,960,068 B2
(45) Date of Patent: Apr. 16, 2024

(54) PORTABLE DEVICE FOR SEMEN QUALITY CONTROL

(71) Applicants: Microfluidlabs Kft., Budapest (HU); Ongo Vettech Kft.

(72) Inventor: Béla Tamás Bábel, Budapest (HU)

(73) Assignees: Microfluidlabs Kft., Budapest (HU); Ongo Vettech Kft., Martonvásár (HU)

( * ) Notice: Subject to any disclaimer, the term of this patent is extended or adjusted under 35 U.S.C. 154(b) by 220 days.

(21) Appl. No.: 17/054,017

(22) PCT Filed: Aug. 16, 2018

(86) PCT No.: PCT/HU2018/050035
§ 371 (c)(1),
(2) Date: Nov. 9, 2020

(87) PCT Pub. No.: WO2019/215463
PCT Pub. Date: Nov. 14, 2019

(65) Prior Publication Data
US 2021/0364770 A1    Nov. 25, 2021

(30) Foreign Application Priority Data
May 10, 2018   (HU) .................................. U1800078

(51) Int. Cl.
*G02B 21/00* (2006.01)
*G01N 33/487* (2006.01)
(Continued)

(52) U.S. Cl.
CPC ....... *G02B 21/0008* (2013.01); *G01N 33/487* (2013.01); *G02B 21/025* (2013.01);
(Continued)

(58) Field of Classification Search
CPC ................ G02B 21/00; G02B 21/0004; G02B 21/0008; G02B 21/0016; G02B 21/0028;
(Continued)

(56) References Cited

U.S. PATENT DOCUMENTS

| 4,896,966 A * | 1/1990 | Boisseau | A61B 5/1105 |
| | | | 382/128 |
| 8,989,597 B2 * | 3/2015 | Treyer | G02B 3/14 |
| | | | 398/88 |

(Continued)

FOREIGN PATENT DOCUMENTS

CN    106018770 A    10/2016

OTHER PUBLICATIONS

Androvision: leaflet "Androvision More Than Casa", minitube, 2019.

*Primary Examiner* — Thong Q Nguyen
(74) *Attorney, Agent, or Firm* — Jason D. Voight

(57) ABSTRACT

A portable device for quality control of semen having a housing and within an inner space of the housing, a battery, a processor and a sample storing device for fixing a sample transporting cell. The device further has a microscope having a camera secured to the housing, an optical device connected to the camera and a light source illuminating the sample transporting cell during use. The sample storing device is arranged in the upper side of the housing or adjacent thereto. The light source is arranged on the outer side of the sample storing device and connected to the housing. The camera is arranged in the inner space of the housing, on the inner side of the sample storing device such that the distance between the supporting plane of the sample storing device and the light sensor of the camera is at most 35 mm.

6 Claims, 2 Drawing Sheets

(51) Int. Cl.
 *G02B 21/02* (2006.01)
 *G02B 21/06* (2006.01)
 *G02B 21/30* (2006.01)
 *G02B 21/36* (2006.01)
(52) U.S. Cl.
 CPC ............ *G02B 21/06* (2013.01); *G02B 21/30* (2013.01); *G02B 21/36* (2013.01)
(58) Field of Classification Search
 CPC ............ G02B 21/0032; G02B 21/0052; G02B 21/0076; G02B 21/008; G02B 21/0088; G02B 21/02; G02B 21/025; G02B 21/06; G02B 21/24; G02B 21/244; G02B 21/245; G02B 21/26; G02B 21/30; G02B 21/34; G02B 21/36; G02B 21/361; G02B 21/362
 USPC .................................................. 359/368–398
 See application file for complete search history.

(56) References Cited

U.S. PATENT DOCUMENTS

| 2011/0090328 | A1* | 4/2011 | Chen | G02B 21/0008 359/383 |
| 2016/0290916 | A1 | 10/2016 | Ben Shoshan et al. | |
| 2017/0227519 | A1* | 8/2017 | Lin | G01N 33/487 |
| 2017/0330321 | A1* | 11/2017 | Hsu | G01N 33/689 |
| 2018/0081157 | A1* | 3/2018 | Monk | G02B 21/0008 |

\* cited by examiner

PORTABLE DEVICE FOR SEMEN QUALITY CONTROL

This is the national stage of International Application PCT/HU2018/050035, filed Aug. 16, 2018.

The present invention relates to a portable device for semen quality control.

BACKGROUND OF THE INVENTION

There is an increasing demand for the in situ analysis of animal and human semen, in particular for the field analysis of the features of semen collected from live stock. The majority of the systems and devices currently available in the market are fixedly installed and therefore the semen samples have to be frozen within the shortest possible time after collection and the samples have to be transported to the place of analysis in a frozen state, where the necessary quality control can be carried out only after melting the sample. Although portable quality control devices are also available in the market, those devices consist of multiple physically separated units which are to be interconnected at the location of sample collection therefore these devices are less suitable for field use. (These devices include, for example, the product AndroVision® of the company Minitube.)

The patent application CN106018770 discloses a portable system for the automatic analysis of the motility and the quality of semen. The system comprises a microscope unit, a light source and a heat insulated reservoir for storing the sample, wherein all of these units are integrated into one device. A separate computing device, for example a laptop or smart phone, can be connected to the microscope unit, said computing device comprising a camera for recording photos or a video, a processing unit and a data storing unit. Instead of the data storing unit it is also possible to store data in the cloud via the internet. Although the individual parts of the system are portable, these part have to be interconnected, synchronized and calibrated before using the system, which makes the use of the system rather complicated, on the one hand, and it can cause compatibility problems and system faults, on the other hand. Moreover, this kind of multiple component systems is not suitable for carrying out a field analysis quickly.

SUMMARY OF THE INVENTION

It is an object of the present invention to provide a portable device for semen quality control that is particularly suitable for field use due to its compact configuration.

The invention is based on the idea that if the microscope unit and the computing processor unit is arranged within the inner space of a small housing, and for the semen sample there is an externally accessible place on the top of the housing or adjacent thereto for sample analysis by the microscope unit, then a device in the form of a single portable unit can be carried out, which is much more compact than the prior art apparatuses. One of the advantages of such a compact portable device is that it can be easily transported to any location, even to a laboratory or to the field (e.g. grazing land, nursing plant, etc.). A further advantage is that for operating the device, there is no need of interconnecting the individual parts thereof at the scene.

The object of the present invention is achieved by providing a portable device for quality control of semen, comprising a housing and within an inner space of the housing, a battery, a processor unit and a sample storing unit for fixing a sample transporting cell, wherein the device is further provided with a microscope unit comprising a camera unit secured to the housing, an optical unit connected to the camera unit and a light source illuminating the sample transporting cell during use. The sample storing unit is arranged inside the housing at the upper side of the housing or adjacent thereto. The light source is arranged on the outer side of the sample storing unit and connected to the housing. The camera unit is arranged in the inner space of the housing, on the inner side of the sample storing unit in such a configuration that the distance between the supporting plane of the sample storing unit and the light sensor of the camera unit is at most 35 mm. The optical unit is arranged between the camera unit and the sample storing unit.

Preferred embodiments of the device according to the invention are defined herein.

BRIEF DESCRIPTION OF THE DRAWINGS

The invention will now be described with reference to the drawings. In the drawings.

DETAILED DESCRIPTION OF THE INVENTION

Figure 1:
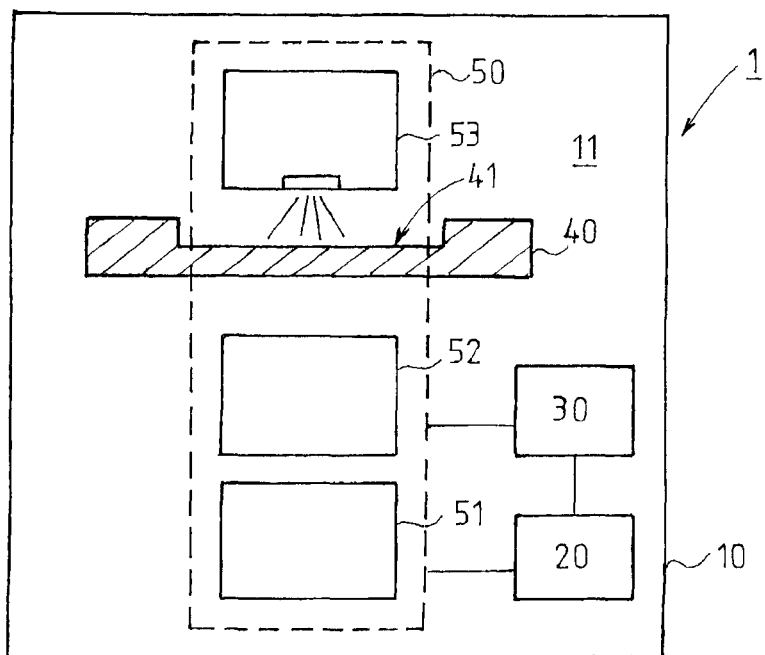
FIG. 1 is a schematic connectivity view of the main units of the portable device according to the invention.

The arrangement of the main units of the portable device 1 according to the invention is schematically illustrated in FIG. 1. The device 1 has a housing 10 preferably made of a material suitable for forming a light-weight, but rigid structure, for example a plastic material. A battery 20, a processor unit 30 and a sample storing unit 40 are arranged in the inner space 11 of the housing 10. The processor unit 30 is configured to control the operation of other units of the device 1, and to process the data resulting from the measurements and to produce the measurement results.

The sample storing unit 40 is arranged at the upper side of the housing 10 or adjacent thereto, inside the housing 10, in such a way that during the use of the device 1 it is permanently accessible from outside, or it can be easily made accessible to the user. The sample storing unit 40 is adapted for fixing a separate sample transporting cell 90. It is noted that although during the use of the device the sample transporting cell 90 containing a semen sample is accommodated in the device 1, the sample transporting cell 90 itself does not form an essential part of the invention.

Additionally, the portable device 1 is further provided with a microscope unit 50 that comprises a camera unit 51, an optical unit 52 and a light source 53. The camera unit 51 is secured to the housing 10. The optical unit 52 is secured to the camera unit 51 and/or the housing 10. Both of the camera unit 51 and the optical unit 52 are arranged in the inner space of the housing 10, adjacent to the inner side of the sample storing unit 40, in such a way that the optical unit 52 is placed between the camera unit 51 and the sample storing unit 40, wherein the distance between a supporting plane 41 of the sample storing unit 40 and a light sensor (e.g. CCD wafer) of the camera unit 51 is at most 35 mm. Due to this small distance, an appropriate definition in depth can be achieved for an analysis with a microscope. The light source 53 is arranged on the top of the sample storing unit 40 in such a configuration that during use it can be capable of illuminating the sample transporting cell 90. As a result, the light source 53 radiates the light towards the inside of the housing 10. The light source is preferably a LED-type light source, but other technologies may also be suitable for providing proper illumination for an analysis with a microscope. The use of the LEDs has the advantage that during the operation they produce a relatively small amount of heat, thereby an undesired warm-up or overheating of the sample transporting cell 90 and the samples stored therein can be avoided.

Figure 2:
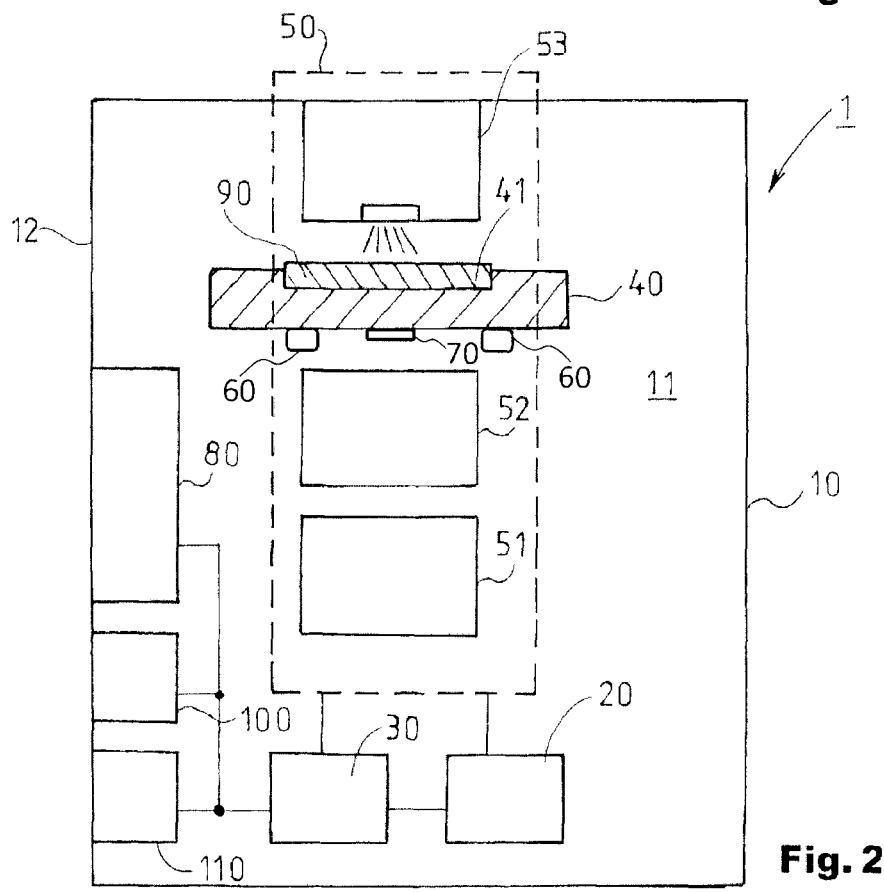
FIG. 2 schematically illustrates a preferred embodiment of the portable device according to the invention, which also includes an additional, supplementary unit as well.

FIG. 2 schematically illustrates a preferred embodiment of the device 1. This embodiment comprises additional parts with respect to the embodiment shown in FIG. 1, wherein the additional parts may be used either individually or in combination.

As shown in FIG. 2, the portable device 1 may, for example, comprise one or more heating elements 60, the operation of which can be controlled by the processor unit 30. The heating elements 60 are preferably arranged on the inner side of the sample storing unit 40. The one or more heating elements 60 are preferably Peltier elements. After switching the heating element 60 on, it warms up the sample storing unit 40, which, in turn, transfers the heat to the sample transporting cell 90 placed therein, and the sample transporting cell 90 further transfers the heat to the sample stored therein, thereby the analysis of a heated sample becomes possible. The heating temperature may be a preset temperature (for example a specific temperature recommended for the sample collected from the examined animal species), or it may be a temperature individually set by the user for the actual analysis.

As shown in FIG. 2, a temperature sensor 70 may be arranged on the sample storing unit 40, preferably mounted on its inner side, wherein the temperature sensor 70 is also controlled by means of the processor unit 30. The temperature sensor 70 is adapted for measuring the actual temperature of the sample storing unit 40 heated by the heating element 60, thereby it is also suitable for indirectly measuring the temperature of the sample.

The portable device 1 according to the invention may further comprise a display 80 arranged on an outer surface 12 of the housing 10 and also coupled to the processor unit 30. Preferably, the display 80 is a touch-screen also allowing manual control of the device.

Figure 3:
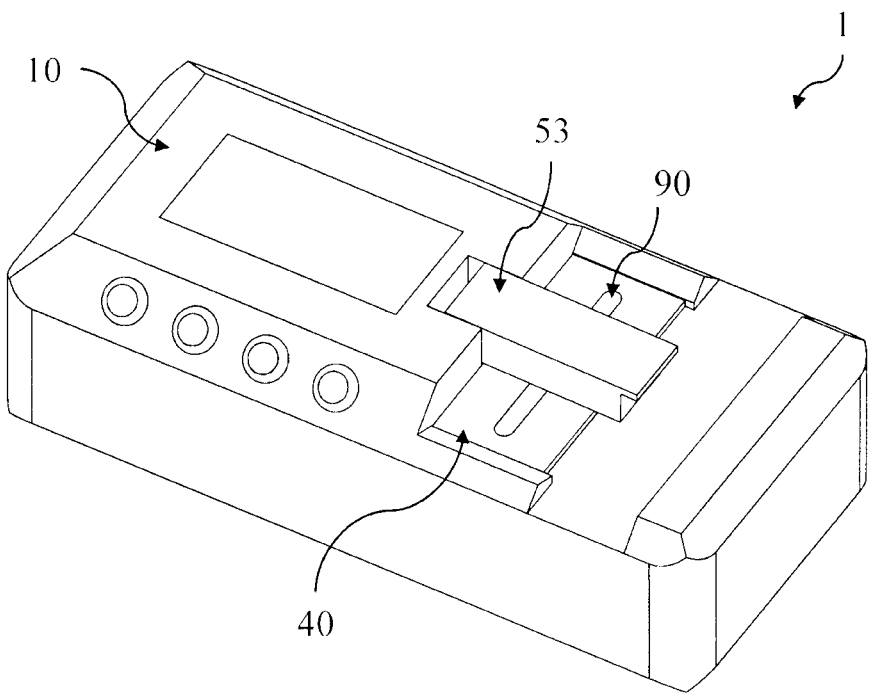
FIGS. 3 and 4 depict a preferred embodiment of the portable device according to the invention, wherein the light source is provided in the form of a panel attached to the housing through a hinge.
Figure 4:
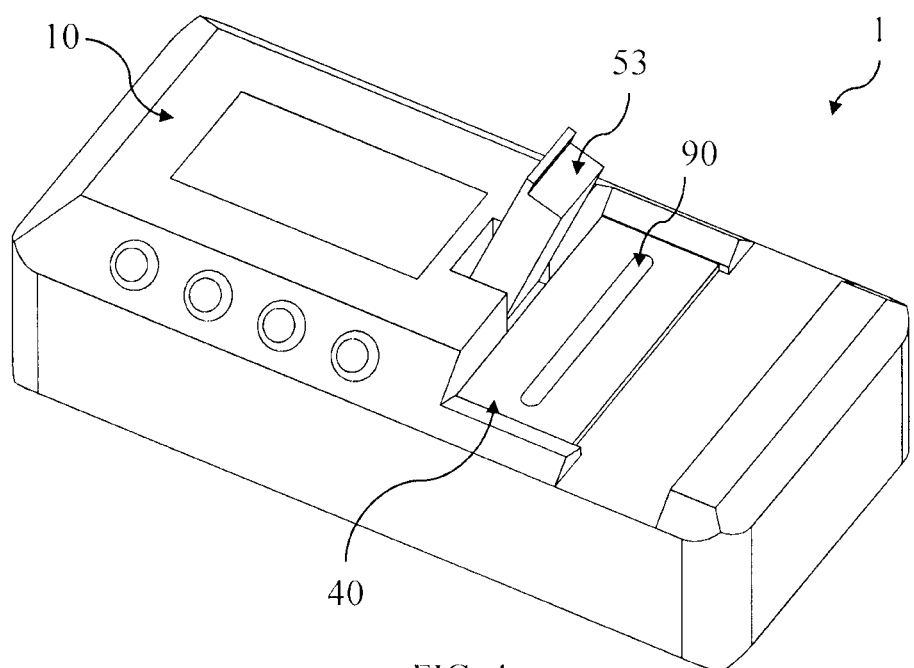

In a preferred embodiment of the portable device 1 (as shown in FIGS. 3 and 4) the light source 53 is formed as a unit that is displaceable with respect to the sample storing unit 40, preferably as a hinged heat panel that can be folded out from the housing 10, or as a unit laterally slidable on the top side of the housing 10. The hinged or the slidable configuration of the light source 53 allows an easy access to the sample storing unit 40 at the insertion or removal of the sample transporting cell 90.

In the portable device 1 according to the invention, the optical unit 52 preferably comprises a liquid lens well known in itself, the operation of which may also be controlled by means of the processor unit 30.

As shown in FIG. 2, the portable device 1 preferably comprises at least one push button 100 as well, and additionally a data communication interface 110, like a USB port. By means of the at least one push button 100, the device can be switched on and off, and in case of multiple push buttons 100, the various functions of the device 1 can be set. By means of the data communication interface 110 the measurement parameters and the measurement result can be saved to an external data storage medium (for example, to an USB pen drive).

The device 1 may further comprise an internal data storage unit. In this case it is not necessary to save the values of the measurement parameters and the measurement results to an external data storage medium after completing the measurements, but the data can be permanently stored in the device 1.

The samples can be analyzed using a so called CASA (computer assisted semen analysis) software or any other custom-tailored software that is suitable for measuring the sample parameters needed for quality control. It is preferred that a software commonly used in the field of technology is applied. The most important parameters of quality control include, for example, the semen concentration (million cells/ml), advancing motility (%) and overall motility (%) of semen cells. The advancing motility is defined as a percentage ratio of those semen cells that move in the same direction at a speed higher than a predetermined speed, to the number of all cells in the sample. The overall motility is defined as the percentage ratio of the amount of all cells that move at a speed above a lower speed threshold, to the number of all cells in the sample. The speed threshold may be different for various species and even for each individual. In addition to the aforementioned analysis parameters, other parameters suitable for quality control and derivable from the existing data can also be used.

The power of the device 1 according to the invention is provided by a battery 20, but the device 1 may also be operated by the mains, and in this case the device can be provided with a mains plug (not shown in the drawings). When the device 1 is energized from the mains, the battery 20 can be automatically charged simultaneously with the operation of the device 1. The charge level of the device 1 may be indicated on the display 80. When the charge level of the battery 20 becomes low, the heating function is first switched off, and later the device 1 can also be shut down.

When using the device 1 according to the invention, the user has to carry out the following steps for the quality control of a sample. After collecting the sample, the user should first place the sample to be inspected into the sample transporting cell 90. The sample transporting cell 90 adapted for the portable device 1 preferably comprises multiple separate compartments, thereby it allows to transport multiple samples at the same time.

The device 1 can be switched on by the push button 100 and then the user can select by means of the display 80 and/or the push button(s) 100 whether to start a heated or a non-heated measurement. In case of a heated measurement, before starting the measurement, the heating element 60 warms up the sample storing unit 40 to a preset temperature or a temperature specified by the user. The device 1 may be configured to continuously indicating the actual temperature on the display 80.

Next the user secures the sample transporting cell 90 with the sample therein to the sample storing unit 40 arranged in the upper part of the housing 10. When the light source 53 is firmly secured to the housing 10, the sample transporting cell 90 can be pushed from the outside into the sample storing unit 40, whereas if the light source 53 is in the form of a slidable or hinged panel, the sample storing unit 40 can be exposed by the displacement of the panel, and the user can insert the sample transporting cell 90 into the device 1 in a much more convenient way.

Once the sample transporting cell 90 has been inserted, the analysis commences automatically or can be manually started, and the microscope unit 50 produces a live image of the sample on the display 80, so the intensity of illumination and the focal length can be set. The adjustment of the definition in depth is essential from the point of view of the proper operation of the evaluation algorithm. The light intensity can be regarded as satisfactory if the streakiness of the camera unit 51 resulted from a weak illumination cannot be seen on the display 80 and the cells can be definitely distinguished from the background. The adjustment of the focal lens can be regarded proper if the contour of the cells appearing on the display 80 is sharp and their color is full black. After properly adjusting the image quality, recording a video can be started. Once the video recording has been finished, the device 1 automatically carries out the analysis of the data and the result of the analysis may immediately be displayed on the display 80.

After showing the results, the user may decide not to conduct further measurements, so the data (the video image and the measurement results) can be saved through the data communication interface 110, e.g. USB port to an external data storage medium (e.g. USB pen drive). However, the user may initiate a new measurement on the same sample, and in this case the former results may be saved to an external data storage medium. After finishing a new measurement the device 1 displays the partial results and any further results deriving from the partial results on the display 80 and these results can also be saved to the connected external data storage medium.

When the sample transporting cell 90 comprises multiple compartments, a separate measurement can be carried out for the sample of each compartment. In this case the partial results associated with the samples (and occasionally an averaged result relating to all of the samples) may be displayed and saved as described above.

In some preferred embodiments of the device 1 according to the invention, the data can be transferred and saved in other ways as well, for example through a wireless connection. The technique of data communication through a wireless connection is well known in the art and therefore its description is omitted here. Furthermore, it is noted that the way of data transfer and data saving in the embodiments described above are mentioned only as examples for those embodiments of the device, and they mean no limitation of the scope of the invention to those embodiments of the device 1.

The type of the electronic connection between the above mentioned units of the portable device 1 and the processor unit 30 (not shown in the drawings) and the way of communication with the processor unit 30 is also well known for a person skilled in the art, so the detailed description thereof is also omitted in the present description.

An advantage of the portable device according to the invention is that it can have small dimensions and it can be formed as a compact analyzing device, and thereby it allows to carry out an in situ analysis conveniently and quickly. The analysis can be performed at the scene right after the collection of the sample, thus the factors adversely influencing the measurement results, like the unfavorable effects of transporting and storing the collected sample, can be significantly reduced.

Another advantage of the device according to the invention is that it can be equally used to analyze human and animal samples. For animal samples the optimum heating temperature associated with the specific species or a particular individual can be set. The analysis of the measurement parameters can also be performed with respect to a specific species or an individual. Analysis of human samples by means of a portable device allows the sample analysis at the home of a patient, thus the device of the invention provides a very cost-effective and convenient solution for carrying out fertility examinations as an alternative to the conventional laboratory examinations.

A further advantage of the portable device of the invention is that after inserting the sample therein, the measurement data can be evaluated, displayed and saved quickly and in a fully automatic way without the need of human intervention.

The invention claimed is:

1. A portable device (1) for quality control of semen, comprising a housing (10) and within an inner space (11) of the housing, a battery (20), a processor (30) and a sample storing device (40) for fixing a sample transporting cell (90), wherein the device (1) is further provided with a microscope (50) comprising a camera (51) secured to the housing (10), an optical device (52) connected to the camera (51) and a light source (53) illuminating the sample transporting cell (90) during use, wherein:
   the sample storing device (40) is arranged inside the housing (10) at an upper side of the housing (10) or adjacent thereto,
   the camera (51) is arranged in the inner space (11) of the housing, on an inner side of the sample storing device (40) facing the inner space (11) of the housing (10) in such a configuration that a distance between a supporting plane (41) of the sample storing device (40) and a light sensor of the camera (51) is at most 35 mm,
   the light source (53) is arranged on an outer side of the sample storing device (40), the outer side of the sample storing device facing outside of the housing (10), the light source being connected to the housing (10) and configured to radiate light towards the inside of the housing onto the sample transporting cell located adjacent to the light source during use,
   the optical device (52) is arranged between the camera (51) and the sample storing device (40),
   the light source (53) is formed as a unit displaceable relatively to the sample storing device (40), in a form of a hinged panel that can be folded out from the housing (10) or a unit laterally slidable along a top of the housing (10).

2. The device according to claim 1, wherein the sample storing device (40) is equipped with a heating element (60) controlled by the processor (30).

3. The device according to claim 1, wherein one or more temperature sensor (70) coupled to the processor (30) is arranged on the sample storing device (40).

4. The device according to claim 1, further comprising a display (80) coupled to the processor (30) and arranged on an outer surface (12) of the housing (10).

5. The device according to claim 1, wherein the optical device (52) is formed by a liquid lens controlled by the processor (30).

6. The device according to claim 1, wherein the light source (53) is displaceable relative to the sample storing device (40) and relative to the camera (51) in the form of a hinged panel that can be folded out from a top of the housing (10) or a unit laterally slidable along a top of the housing (10).

* * * * *